United States Patent [19]

Redmore et al.

[11] 4,139,718
[45] Feb. 13, 1979

[54] POLYVINYL QUATERNARIES

[75] Inventors: Derek Redmore, Ballwin; Frederick T. Welge, Affton, both of Mo.

[73] Assignee: Petrolite Corporation, St. Louis, Mo.

[21] Appl. No.: 442,317

[22] Filed: Feb. 14, 1974

[51] Int. Cl.² .................... C07C 85/02; A01N 9/20
[52] U.S. Cl. .................. 260/567.6 P; 260/567.6 M; 424/329
[58] Field of Search ............... 260/567.6 M, 567.6 P

[56] References Cited

U.S. PATENT DOCUMENTS

| 2,817,664 | 12/1957 | Cavallito et al. | 260/567.6 M |
| 3,424,793 | 1/1969 | Kokosinki et al. | 260/567.6 M |
| 3,557,214 | 1/1971 | Koenig et al. | 260/567.5 M |

*Primary Examiner*—James O. Thomas, Jr.
*Assistant Examiner*—James H. Reamer
*Attorney, Agent, or Firm*—Sidney B. Ring; Hyman F. Glass

[57] ABSTRACT

This invention relates to vinyl quaternaries and polymers thereof; and to the preparation thereof from ethylene dihalides and tertiary amines.

6 Claims, No Drawings

POLYVINYL QUATERNARIES

When ethylene dihalides react with tertiary amines, one expects the following reaction to occur which yields diquaternaries $$R_3N + XCH_2CH_2X \rightarrow R_3N^{\oplus}CH_2CH_2N^{\oplus}R_3 \cdot 2X^{\ominus} \quad \text{(Eq. I)}$$

We have now discovered that the above reaction occurs more readily with certain amines than with other amines. For example, although pyridines yield diquaternaries according to Equation I in high yields, amines such as dimethylalkyl amines tend to yield vinyl quaternaries which then polymerize to yield polyvinyl quaternaries according to the following equation:

$$\begin{array}{c} R \\ R'N \\ R \end{array} + XCH_2CH_2X \longrightarrow \begin{array}{c} R \\ R'N^{\oplus}CH_2CH_2X \\ R \end{array} \longrightarrow \quad \text{(Equation II)}$$

$$\begin{array}{c} R \\ R'N^{\oplus}-CH=CH_2 \\ R \end{array} \longrightarrow \begin{array}{c} +CH-CH_2+_n \\ | \\ RN^{\oplus}R \cdot X^{\ominus} \\ | \\ R' \end{array}$$

The overall reaction is $$2 \begin{array}{c} R \\ R'N \\ R \end{array} + XCH_2CH_2Cl \longrightarrow \quad \text{(Equation III)}$$

$$\begin{array}{c} R \\ R'N^{\oplus} \\ R \\ H \end{array} Cl^{\ominus} + \begin{array}{c} +CH_2-CH_2+_n \\ | \\ RN^{\oplus}R \ X^{\ominus} \\ | \\ R' \end{array}$$

In addition, we have discovered that certain amines such as triethyl amine, tributylamine, dimethyl aniline, etc. tend to produce vinyl halide because hydrogen rather than carbon attack predominates according to the following equation:

$$R_3N + XCH_2CH_2X \rightarrow R_3N^{\oplus}H \cdot Cl^{\ominus} + CH_2=CHX \quad \text{(Eq. IV)}$$

In general, the polyvinyl quaternaries of this invention are prepared in the following manner. A solution of about 2 moles of tertiary amine is reacted with 1 mole of the ethylene dihalide at a temperature of at least about 100° C. such as from about 100° to 200°, for example from about 120° to 180°, but preferably from about 130° to 170° for a period of at least about 2 hrs., for example from about 3 to 15 hrs., but preferably from about 4 to 12 hrs. An aqueous solvent is preferably employed, i.e., water or water in combination with a water miscible solvent such as alcohols, etc. In contrast, where a solvent is not employed, the usual product is the diquaternary.

The preferred tertiary amines employed in this invention are those of the formula $$\begin{array}{c} CH_3 \\ | \\ R-N \\ | \\ CH_3 \end{array}$$

where R preferably has at least 6 carbon atoms, such as from 6–30 carbon atoms, for example from 8–20 carbon atoms, but preferably from 12–18 carbon atoms. R is preferably aliphatic for example alkyl, alkenyl, etc., mixtures thereof, etc.

Because of availability, the preferred ethylene dihalide is ethylene dichloride.

The products of this invention have a wide variety of uses such as corrosion inhibitors, flocculants, microbiocides, etc.

The following examples illustrate the invention.

EXAMPLE 1

To a 1 pint Chemco reactor was charged a mixture of ethylene dichloride (49.5g; 0.5 mole), dimethyl cocoamine (213g; 1 mole) and water (262.5g). This mixture was heated at 125°–160° for 3 hours and then allowed to cool. Analysis of the product gave the following results:

Chloride, 6.5% (0.96 equivalents), Acid Number: 45.6 (0.43 equivalents).

Basification to pH 8 of 82.5g of the reaction solution and extraction with ether yielded 18g of dimethylcocoamine. The aqueous solution contained the polyvinyl quaternary amine identified by the following NMR spectrum.

0.88 (3H), 1.3 (20H), 2.8 (2H), 3.23 and 3.4–3.8 (8H) 3.8–4.4 (1H). NO vinyl hydrogens in the spectrum.

$$\begin{array}{c} 3.8-4.4 \quad 2.8 \\ [-CH-CH_2-]_n \\ | \\ CH_3-N^+-CH_3 \ Cl^- \\ | \\ CH_2(CH_2)_{10}CH_3 \\ 3.4-3.8 \quad 1.3 \quad 0.88 \end{array}$$

The reaction product is therefore described in the equation:

$$2 \ C_{12}H_{25}N(CH_3)_2 + ClCH_2CH_2Cl \longrightarrow$$

$$C_{12}H_{25}N^{\oplus}(CH_3)_2 + [-CH-CH_2-]_n$$
$$H \quad Cl^{\ominus} \quad CH_3NCH_3 \ Cl^{\ominus}$$
$$\quad \quad \quad \quad \quad \quad | $$
$$\quad \quad \quad \quad \quad \quad C_{12}H_{25}$$

EXAMPLE 2

This example illustrates the use of a different solvent system.

Dimethyl cocoamine (213g), ethylene dichloride (49.5g) water (131g) and isopropanol (131g) were heated at 130°–152° for 20 hours. Analysis of the resulting solution showed 96% of the available chloride ion was formed and by base titration that 45% of the amine charged was present as amine hydrochloride. The product is virtually identical to that of Example 1.

EXAMPLE 3

By the procedure of Example 1, dimethyl tetradecylamine was reacted with ethylene dichloride in water at 130°–150°. After 2 hrs. the formation of ionic chloride was 99% complete with exactly half of the chloride present as amine hydrochloride and the other half of the chloride as polyvinylammonium chloride.

EXAMPLE 4

Dimethyloctadecylamine (148.5g; 0.5 mole), ethylene dichloride (24.8g; 0.25 mole) and water (173g) were heated in a 1 pint Chemco reactor at 160°–172° for 4 hours. The product gave a chloride analysis of 5.2% (100% reaction) and acid value of 43 mg KOH/g (50% amine hydrochloride). NMR indicated the quaternary product to a polyvinylammonium quaternary.

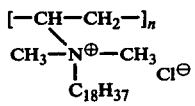

We claim:

1. The process for preparing polyvinyl quaternary amines which comprises reacting an aqueous solution of a tertiary amine with ethylene dihalide in the mol ratio of about 2 to 1 at a temperature of at least about 100° C. for a time sufficient to produce a vinyl quaternary amine, the tertiary amine being of a structure such that under the conditions of the reaction it is capable of both adding to one end of the ethylene dihalide and causing dehydrohalogenation to yield a vinyl quaternary amine, and continuing the reaction so that the vinyl quaternary amine is further polymerized to form the polyvinyl quaternary, the amine being a dimethyl aliphatic hydrocarbon amine where the aliphatic hydrocarbon group has 6 to 30 carbon atoms.

2. The process of claim 1 where the tertiary amine is

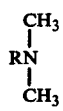

where R is alkyl of 8-20 carbon atoms and the temperature is 100° to 200° C.

3. The process of claim 2 where the tertiary amine is

where R is an alkyl group having about 12 to 18 carbon atoms, the reaction temperature is 120° to 180° C., and the solvent component of the aqueous solution is water or water in combination with a water miscible alcohol.

4. The process of claim 1 where the ethylene dihalide is ethylene dichloride.

5. The process of claim 2 where the ethylene dihalide is ethylene dichloride.

6. The process of claim 3 where the ethylene dihalide is ethylene dichloride.

* * * * *